United States Patent [19]
Fury

[11] Patent Number: 5,431,633
[45] Date of Patent: Jul. 11, 1995

[54] NONINVASIVE DEVICE FOR PREVENTING PRESSURE BUILD-UP IN PLEURAL SPACE AND REDUCING POSSIBILITY OF DEVELOPMENT OF A TENSION PNEUMOTHORAX FROM AN OPEN PNEUMOTHORAX

[75] Inventor: Paul K. Fury, Houston, Tex.
[73] Assignee: Global Fury, Inc., Houston, Tex.
[21] Appl. No.: 239,367
[22] Filed: May 6, 1994
[51] Int. Cl.$^6$ ............................................. A61M 1/00
[52] U.S. Cl. ................................... 604/122; 128/888
[58] Field of Search ................. 604/122; 128/888, 889

[56] References Cited

U.S. PATENT DOCUMENTS

| | | | |
|---|---|---|---|
| 1,319,299 | 10/1919 | Meehan | 128/888 |
| 3,782,378 | 1/1974 | Page | 128/888 |
| 4,465,062 | 8/1984 | Versaggi et al. | 128/1 R |
| 4,717,382 | 1/1988 | Clemens et al. | 604/122 |
| 5,090,406 | 2/1992 | Gilman | 128/888 |
| 5,160,322 | 11/1992 | Scherem et al. | 604/122 |
| 5,195,977 | 3/1993 | Pollitt | 604/122 |
| 5,263,922 | 11/1993 | Sova et al. | 602/59 |

Primary Examiner—Paul J. Hirsch
Attorney, Agent, or Firm—Maryam Bani-Jamali

[57] ABSTRACT

This invention provides a method and a noninvasive device for preventing pressure build-up in pleural space and reducing possibility of development of tension pneumothorax from open pneumothorax by providing a rigid, tubular base firmly attached to an annular flange and a noninvasive, flexible, pliable sheet with a central aperture for closing a sucking chest wound of a patient, while providing a possible path for discharging air, body fluids or any combination thereof from the pleural space of a patient. A generally flat, one-way check valve for allowing air discharge is located in the tubular base. A protective, tubular cover comprises a screening means and is used for protecting the check valve from foreign debris while allowing exit of air, body fluids or any combination thereof from the check valve and enabling visual monitoring of fluid levels within the device.

11 Claims, 7 Drawing Sheets

NONINVASIVE DEVICE FOR PREVENTING PRESSURE BUILD-UP IN PLEURAL SPACE AND REDUCING POSSIBILITY OF DEVELOPMENT OF A TENSION PNEUMOTHORAX FROM AN OPEN PNEUMOTHORAX

BACKGROUND OF THE INVENTION

1. Field of the Invention

This invention relates generally to a method and a noninvasive device for treating a chest injury and more specifically relates to a method and a noninvasive device for preventing pressure build-up in pleural space (a potential space between parietal and visceral pleuras) of an open pneumothorax (a sucking chest wound), avoiding conversion of a simple pneumothorax into a tension pneumothorax (a magnified version of the simple pneumothorax).

2. General Background

The present invention relates to a method and a noninvasive device for preventing pressure build-up in pleural space of an open pneumothorax, in order to reduce possibility of development of a tension pneumothorax. The open pneumothorax may usually result from an opening on a side in a chest adjacent to a lung caused by a gunshot, knife wound, motor vehicle accident and sometimes fall or other injury accident. The opening caused by the wound creates a path for outside air, body fluids or any combination thereof to flow into thoracic cavity. Since air, body fluids or any combination thereof entering the thoracic cavity through the wound may flow into a pleural space and may not enter the lung, the lung may not be able to inflate properly. Thus, an open chest wall may eventually cause a collapse of the lung on the side of the opening, creating the tension pneumothorax. With movement of air, body fluids or any combination thereof in and out of the open chest wall, some air, body fluids or any combination thereof may be trapped in the pleural space adjacent to the lung on the side of the opening, and the lung and some great veins leading to heart may be compressed. As a result, there may be shortness of breath. In addition, existing atmospheric air, body fluids or any combination thereof in the chest wall may bring contaminants into the chest.

If air, body fluids or any combination thereof enters but does not leave the pleural space, a life-threatening situation may arise. A tension pneumothorax develops as pressure in the pleural space exceeds atmospheric pressure. The physiologic consequences of the tension pneumothorax are similar to a simple pneumothorax, but on a magnified scale. Increasing pressure in the pleural space causes the lung on the side of the wound to collapse. Thus, breathing becomes increasingly difficult and, as a result of a decreasing blood flow into the heart, a number of shocks may occur.

In order to reduce the possibility of the development of the tension pneumothorax, the opening in the chest wall preferably should be normally closed while allowing an outflow of air, body fluids or any combination thereof from the pleural space. Until recently, the opening in the chest wall has been usually treated using Saran (a trademark for identifying a thin plastic sheet) wrap, or using a Vaseline (a registered trademark for identifying a product) gauze covered with sterile gauze, or utilizing an aluminum foil or any other type of occlusive dressing secured with tape so as to seal the wound. However, such methods of treatment may be inefficient if a hole exists in the lung and if the wound is sealed externally since air, body fluids or any combination thereof may enter the pleural space through the hole in the lung and produce a pressure build-up within the pleural space. None of the above listed methods would be capable in such a case to provide an efficient, easy-to-use and easy-to-clean one-way check valve for decreasing the pressure build-up within the body of the patient and for facilitating the outflow of air, body fluids or any combination thereof from the pleural space.

Another recommended method for reducing the possibility of development of tension pneumothorax has been to utilize a valve effect by closing the opening in the chest through the creation of a valve using a dressing while taping only three sides of the dressing, so that any extra air, body fluids or any combination thereof is discharged through the opening. However, the valve effect of the dressing may be neutralized during emergency treatment of the patient, due to location of the wound compared to position of the patient during transportation, due to interference of applied support apparatus with operation of the valve, or due to application of a spine board or of belts or of other emergency equipment.

Depending upon size of the wound, some other methods have been recommended, such as: (a) a condom method comprising taping a condom with an open end and with a closed tip over the wound and cutting off the closed tip of the condom to allow exit of air, body fluids or any combination thereof from the pleural space for smaller wounds, or (b) a glove method comprising using a plastic or rubber glove for covering the wound and cutting off a closed tip of one finger of the glove to allow exit of air, body fluids or any combination thereof from the pleural space for larger wounds. The condom method or the glove method, however, may not be efficient methods since under some circumstances substantial back flow of air, body fluids or any combination thereof into the pleural space may exist, and under other occasions the tip that is cut off may be too small to allow sufficient discharge of air, body fluids or any combination thereof causing pressure build-up in the pleural space.

3. Description of the Prior Art

In the past few years, there have been some improvements in the prior methods of reducing the possibility of development of tension pneumothorax from open pneumothorax by using Vaseline gauzes, plastic wraps, aluminum foils, and other similar wraps. A few patents have been recently registered which explain methods for reducing the possibility of the development of tension pneumothorax. Such patents disclose the use of a one-way check valve to facilitate the expelment of air, body fluids or any combination thereof trapped in the pleural space.

Versaggi et al., U.S. Pat. No. 4,465,062, describes a noninvasive seal for protecting a sucking chest wound using a one-way check valve. The Versaggi valve is located in close proximity to the wound, creating the possibility of interference of fluid from the wound with the operation of the valve. In addition, the seal may have to be removed in case of abundant gathering of fluid in the valve of the Versaggi seal in order to allow removal of the collected fluid from the valve. Each removal of the seal may result in additional collection of air, body fluids or any combination thereof in the pleural space, threatening the patient further. Also, a hollow dome-shaped cap covers the valve, said cap being attached to a bandage base by means of an adhesive located on the upper surface of the base, causing the dome-shaped cap to be fixably attached to the base and delaying any need of removal of collected fluid from the valve.

Clemens et al., U.S. Pat. No. 4,717,382, also describes a noninvasive apparatus for treating a sucking chest wound. Clemens et al. uses adjustable straps to hold the apparatus against the body of the patient and over the wound. Adjustable straps may have several disadvantages in treating the wound. Firstly, variable lengths of strap may be needed to place the apparatus in position on the body of the patient. Secondly, the apparatus may not be in a sufficiently stable and fluid-tight relationship to the wound due to movements of the patient and outflow of air, body fluids or any combination thereof from the pleural space. With medical industry welcoming disposable medical instruments, a final disadvantage of Clemens et al. is the factor that the apparatus is sterilized and reused. Therefore, the application of the apparatus of Clemens et al. may be limited to a certain extent.

Scheremet et al., U.S. Pat. No. 5,160,322, patents an occlusive chest sealing valve used in the emergency closing of an open thoracic wound. Scheremet et al. includes a rigid annular base member (as opposed to a tubular base used in the present invention) permanently secured to a flexible attachment. The tubular base used in the present invention may be more efficient than the annular base member used in Scheremet et al. since the tubular base is not directly attached to the body of the patient. A distance is created between the body of the patient and the tubular base in the present invention, due to the existence of a middle layer and an annular flange between the body and the tubular base, and due to the existence of a bottom part and a middle part of the tubular base between the middle layer and the check valve since the tubular base, rather than the annular base, is being used. In Scheremet et al., the valve and base member are relatively thin and define a top surface disposed in closely spaced relation above the attachment means surrounding the opening of the wound. Also, Scheremet et al. has a dome-shaped housing with spaced cut-out openings on periphery of the housing, such openings forming support struts around the periphery of the housing. In the present invention in contrast, the cover is tubular, with a top surface and a screening means across the top surface, said screening means providing a larger surface area for the exit of air, body fluids or any combination thereof from the pleural space than the surface area provided by Scheremet et al. while protecting the valve from foreign debris and contaminants.

Sova et al., U.S. Pat. No. 5,263,922, protects a valved bandage specifically relating to a device and method for covering an open chest wound. Sova et al. utilizes a self-closing one-way valve section secured over a hole in a sheet used for closing the open chest wound. A disadvantage of Sova et al. lies in attaching the valve to the sheet. Thus, if any clogging results in the valve, the device has to be removed, creating additional flow of air or foreign debris or body fluids or any combinations thereof into the pleural space. In addition, a sufficient amount of pressure from air, body fluids or any combination thereof into the valve is needed in Sova et al. to overcome the resilient force of a spring strip which operates the valve.

SUMMARY OF THE INVENTION

A primary object of this invention is to provide a method and a noninvasive device for preventing pressure build-up in a pleural space and for reducing possibility of development of a tension pneumothorax from an open pneumothorax (a sucking chest wound), by providing a method and a device to close the wound, such that possibility of flow of air, body fluids or any combination thereof from outside into the pleural space is reduced but the outflow of air, body fluids or any combination thereof accumulated inside the pleural space is facilitated.

An object of this invention is to provide a method and a noninvasive device for preventing pressure build-up in the pleural space and for reducing possibility of development of a tension pneumothorax from an open pneumothorax, by providing a method and a device to close the wound, such that possibility of flow of air, body fluids or any combination thereof from outside into the pleural space is reduced but an exit pathway for discharging air, body fluids or any combination thereof from the pleural space out of the body is provided.

Another object of this invention is to provide a normally closed valve to preferably keep the wound normally closed, with the valve opening in response to a force from air, body fluids or any combination thereof flowing from inside of the pleural space into and out of the valve, in order to efficiently allow air, body fluids or any combination thereof to exit the body.

Still another object of this invention is to present a device which is disposable.

A further object of this invention is to provide a method and a noninvasive device for preventing pressure build-up in the pleural space and for reducing possibility of development of a tension pneumothorax from an open pneumothorax, such that a valve is used that may be easily removable for cleaning or replacement during operation if needed, without substantially effecting flow of air, body fluids, contaminants or any combinations thereof, from outside into the pleural space.

Another object of the invention is to provide a method and a noninvasive device for preventing pressure build-up in the pleural space and for reducing possibility of development of a tension pneumothorax from an open pneumothorax, such that a noninvasive, flexible, pliable sheet is used which is easily attachable to the body of the patient on different locations as required, while having capability of being temporarily fixed in a stable manner during utilization and being easily removed when necessary.

An additional object of this invention is to provide an optimum drainage of air, body fluids or any combination thereof from inside the pleural space by using a tubular cover, with a top surface having a number of openings, said tubular cover being easily removable, rotatable and adjustable, such that discharge of air, body fluids or any combination thereof from the pleural space out of the body may be varied relatively easily.

A final object of this invention is to provide a tubular base under the valve in order to create a distance between the valve and the body of the patient, wherein the valve is positioned at least at such distance from the wound to prevent or reduce possibility of interference of air, body fluids or any combination thereof with operation of the valve and to facilitate cleaning or replacement of the valve.

Additional objects and advantages of the invention will be set forth in part in a detailed description which follows, and in part will be obvious from the description, or may be learned by practice of the invention.

This invention provides a method and a noninvasive device for preventing pressure build-up in pleural space and reducing possibility of development of tension pneumothorax from open pneumothorax by providing a rigid, tubular base firmly located on a noninvasive, flexible, pliable sheet with a central aperture for closing a sucking chest wound of a patient, while providing a possible path for discharging air, body fluids or any combination thereof from the pleural space of the patient. This invention comprises: a noninvasive, flexible, pliable sheet with a central aperture, said aperture being located across the wound, said sheet used for attaching the device to tile body of the patient and comprising a top layer, a middle layer, and a bottom layer, said middle layer located between the top layer and the bottom layer, said bottom layer being easily removable and covering the middle layer; a rigid, tubular base comprising a bottom part, a middle part and a top part, with a ring horizontally encircling the bottom part and extending as an integral component of the bottom part and located between the top layer of the sheet and an annular flange, such that the tubular base does not touch the body of the patient, and the annular flange placed between the ring of the tubular base and the middle layer, with the middle layer capable of being easily, efficiently and quickly attached to and then removed from the body of the patient upon removal of the bottom layer, such that the aperture in the sheet is placed in alignment with an opening of the wound upon attachment; a generally flat, one-way check valve located above the middle part of the tubular base, said check valve used to prevent pressure build-up in the pleural space; and a protective, tubular cover comprising a top surface and a tubular surface, said top surface having openings which serve as a screening means, the protective, tubular cover used for protecting the check valve from foreign debris while allowing exit of air, body fluids or any combination thereof from the check valve and enabling visual monitoring of fluid levels within the device. It is to be understood that the descriptions of this invention are exemplary and explanatory, but are not restrictive, of the invention.

BRIEF DESCRIPTION OF DRAWINGS

The accompanying drawings, which are incorporated in and constitute a part of this specification, illustrate examples of preferred embodiments of the invention and, along with the description, serve to explain the principles of the invention. The same characters of reference are employed in the drawings to indicate corresponding similar parts throughout the several figures of the drawing.

DETAILED DESCRIPTION OF THE PREFERRED EMBODIMENT

Figure 2:
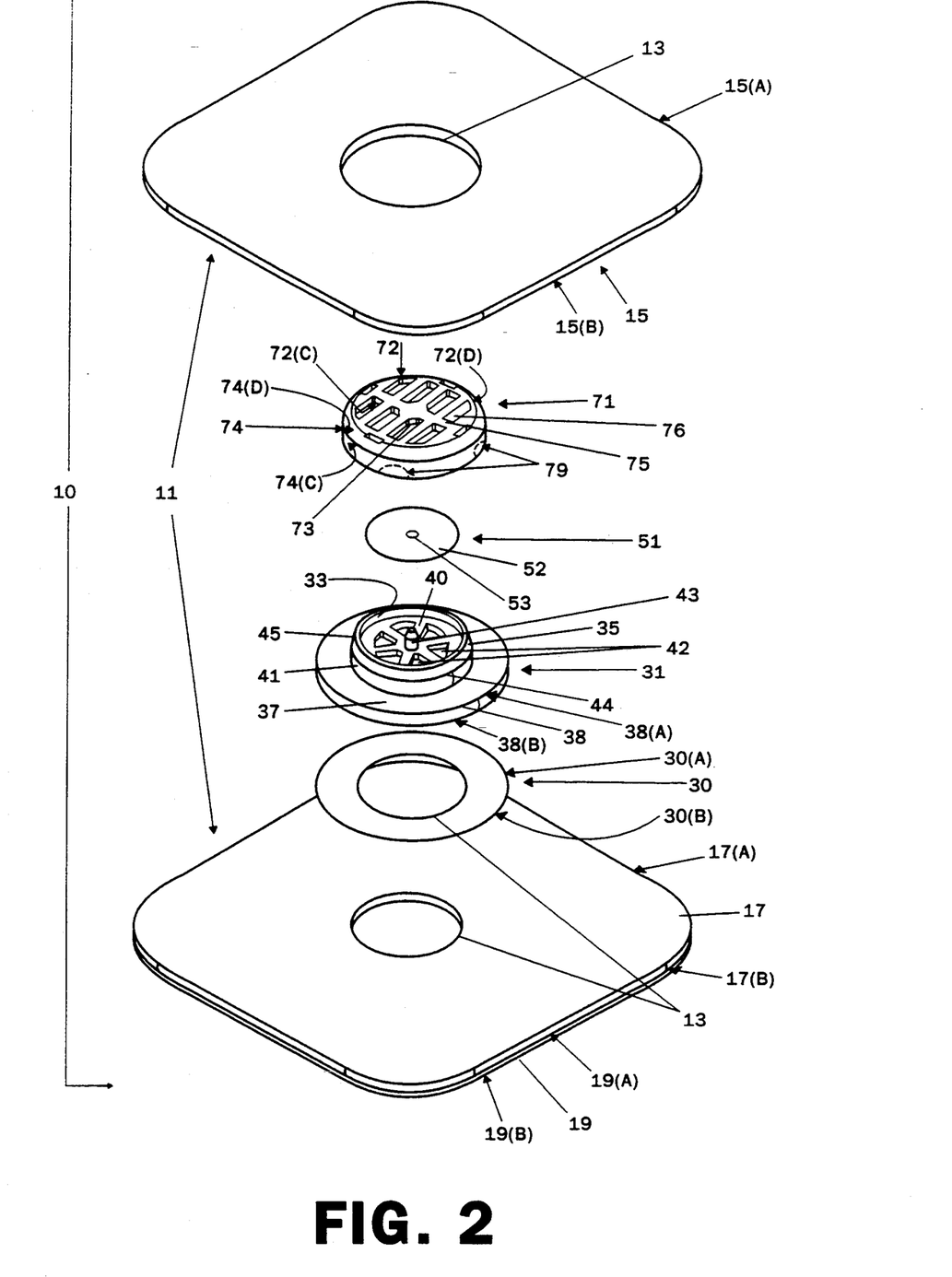
FIG. 2 is an exploded perspective view of the invention in FIG. 1.

A preferred embodiment of the present invention is illustrated in the attached drawings. The drawings illustrate a noninvasive device 10 for preventing pressure build-up in pleural space and reducing possibility of development of a tension pneumothorax from an open pneumothorax or a sucking chest wound 91, as commonly known. As indicated in FIG. 2 and in the other drawings, the device 10 comprises a noninvasive, flexible, pliable sheet 11, a rigid, tubular base 31, a generally flat, one-way check valve 51, and a protective, tubular cover 71. Preferably, an annular flange 30 may also be included under the rigid, tubular base 31.

The noninvasive, flexible, pliable sheet 11 and the annular flange 30 preferably include a central aperture 13, comprising a circular or elliptical shape. The sheet 11 preferably may comprise four edges, four curved comers, and three layers. The sheet 11 comprises a top layer 15, a middle layer 17, and a bottom layer 19, with the top layer 15 being on top of the sheet 11 and the middle layer 17 being adjusted between the top layer 15 and the bottom layer 19. The rigid, tubular base 31 should have an inside 33 and an outside 35. Most preferably, the tubular base 31 comprises a bottom part 37, a middle part 41 and a top part 45. A ring 38 encircles the bottom part and extends horizontally from the outside 35 of the bottom part 37 and as an integral component of the bottom part 37 of the tubular base 31, the ring 38 being positioned between the top layer 15 and the annular flange 30. The annular flange 30 preferably extends horizontally between the ring 38 and the middle layer 17 of the sheet 11.

Figure 4:
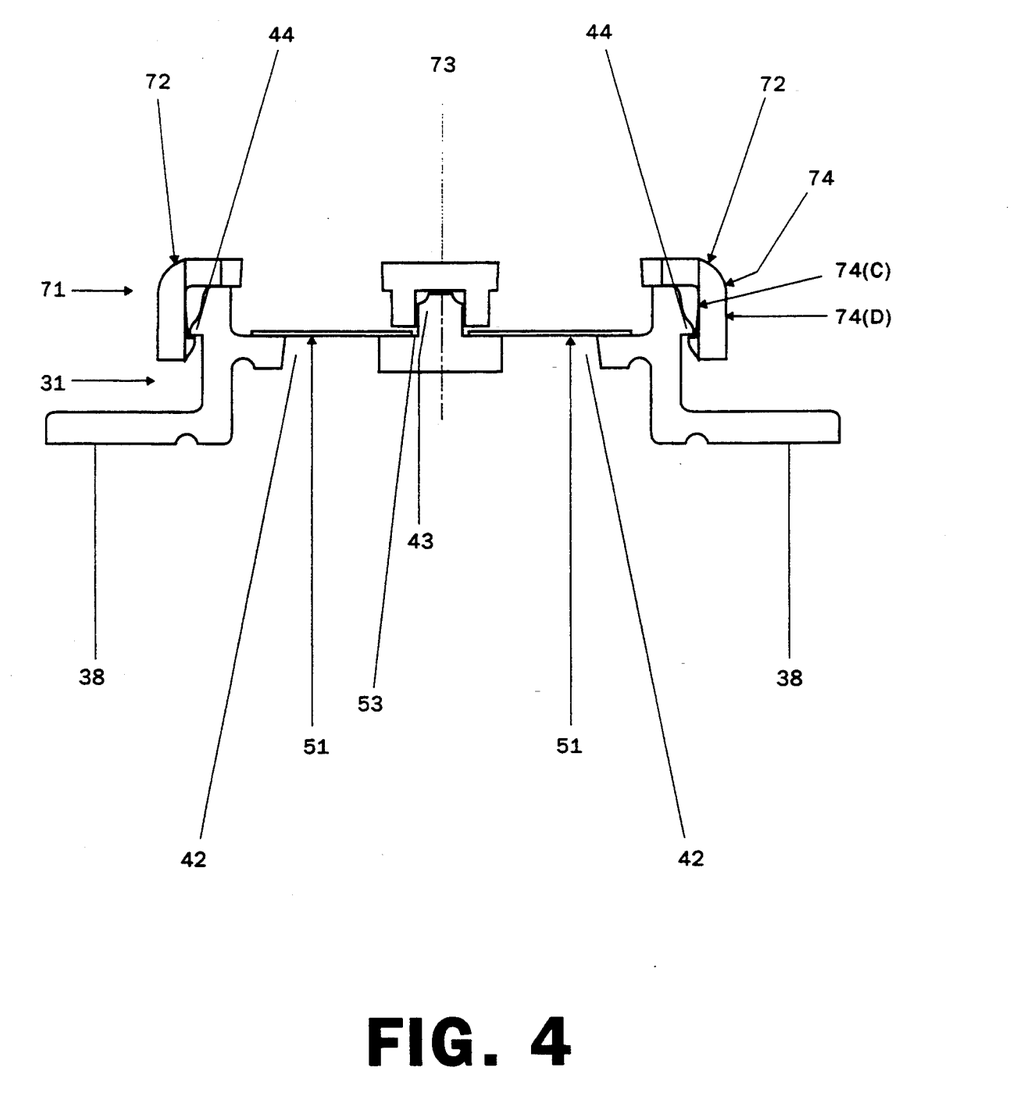
FIG. 4 is a cross-sectional view of the rigid, tubular base, the generally flat, one-way check valve, and the protective, tubular cover in FIG. 1 through the check valve (in closed position)

Each layer, the annular flange 30, and the ring 38 have a top surface (A) and a bottom surface (B). An adhesive material covers the bottom surface 15(B) of the top layer 15 or the top surface 38(A) of the ring 38 of the tubular base 31 in order to attach the bottom surface 15(B) of the top layer 15 to the top surface 38(A) of the ring 38. In addition, an adhesive material covers the bottom surface 38(B) of the ring 38 or the top surface 30(A) of the annular flange 30, such that the annular flange 30 is in a fixed position under the bottom surface 38(B) of the ring 38 and above the top surface 17(A) of the middle layer 17. In such a position, the ring 38 and the annular flange 30 assist in holding the tubular base 31 vertically and upwardly in a permanent position. The bottom surface 30(B) of the annular flange 30 or the top surface 17(A) of the middle layer 17 may be covered by an adhesive material to attach the bottom surface 30(B) of the annular flange 30 to the top surface 17(A) of the middle layer 17. The bottom surface 17(B) of the middle layer 17 is preferably covered with a temporarily adhesive material for temporarily attaching the bottom surface 17(B) of the middle layer 17 to the top surface 19(A) of the bottom layer 19. Preferably, the bottom layer 19 should be easily removable. The temporarily adhesive material should allow the top surface 19(A) of the bottom layer 19 to be easily, efficiently and quickly removable from the bottom surface 17(B) of the middle layer 17. Also, the temporarily adhesive material should preferably allow the bottom surface 17(B) of the middle layer 17 to be easily, efficiently and quickly adhered to and easily, efficiently and quickly removed from a body 95 of a patient 93 in surrounding relationship to the wound 91. It is worthy to note that the adhesive material that shall preferably be used in this invention comprises hypoallergenic component(s) and may be sterilized, such adhesive material conforming with Tripartite Biocompatibility Test for Medical Devices up to body fluid contact. Any medical device not meeting such FDA tests is not marketable in United States. This device 10 is engineered to most preferably conform to FDA requirements in this area. Also, a large percentage of the present invention preferably comprises double-sided high density polyethylene, which may be burned for disposal without hazardous pollutants being emitted into the atmosphere.

The central aperture 13 may preferably run in alignment through the top layer 15, the ring 38, the annular flange 30, the middle layer 17 and the bottom layer 19. The aperture 13 should preferably be in alignment with an opening 97 of the wound 91 when the sheet 11 is adhered to the body 95 of the patient 93.

Figure 5:
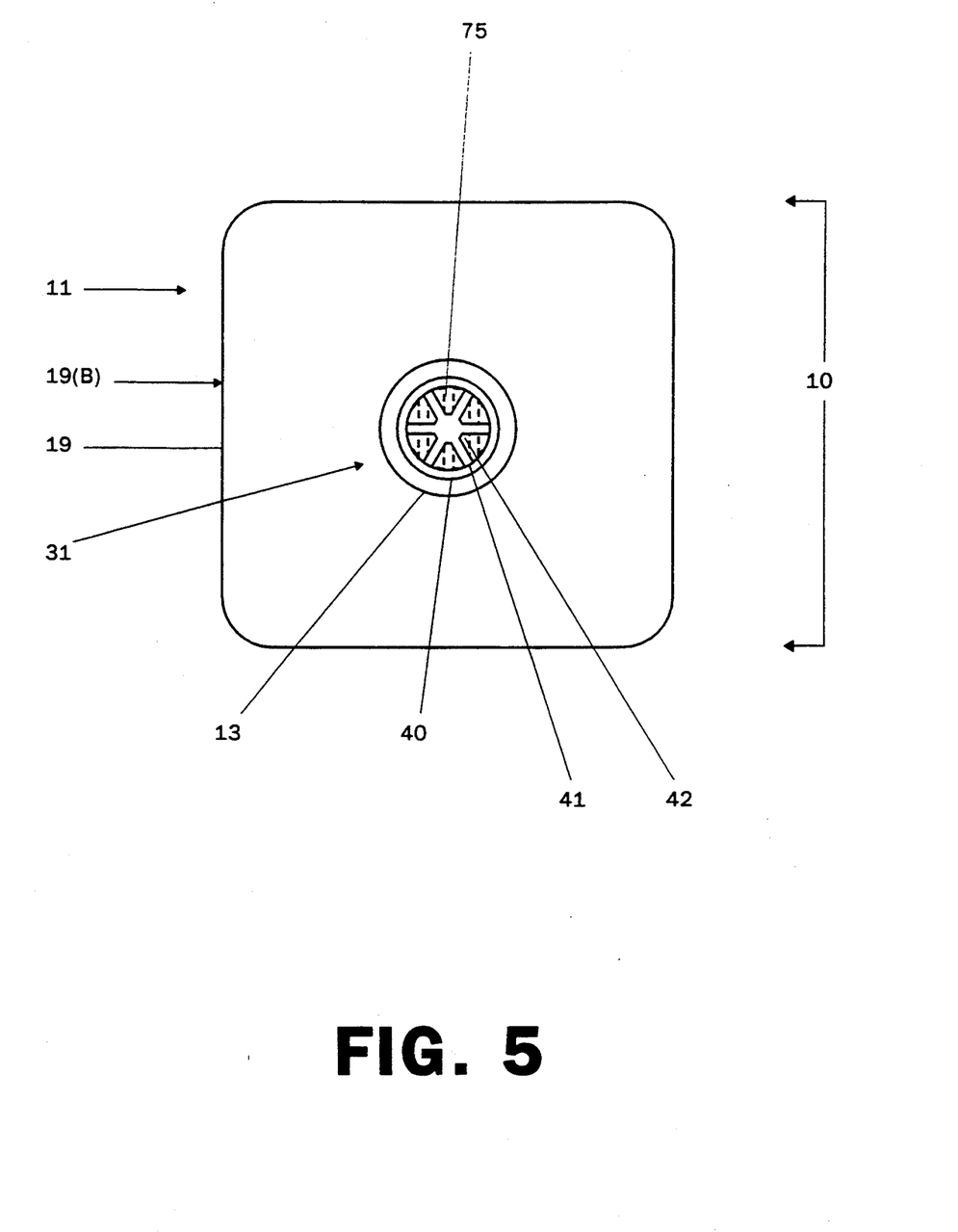
FIG. 5 is a bottom view of the present invention (in closed position) showing the valve base and indicating by dotted lines the tubular cover.

A valve base 40 extends across the inside 33 of the middle part 41 of the tubular base 31 as an integral part of the tubular base 31. The valve base 40 preferably comprises openings 42 to permit air, body fluids or any combination thereof to escape from the wound 91. In addition, the valve base 40 may comprise a small, integral, central post 43 extending vertically and upwardly from the valve base 40. Also, a thin, annular rim 44 preferably runs around the outside 35 of the middle part 41 of the tubular base 31.

The generally flat, one-way check valve 51 most preferably comprises a lightweight, flat, flexible disc 52 with a small, central hole 53. The one-way check valve 51 may also be transparent. The check valve 51 is most preferably located on the valve base 40 extending inside 33 the middle part 41 of the tubular base 31. In addition, the small, central post 43 extending upwardly from the valve base 40 preferably passes through the central hole 53 of the check valve 51.

Figure 1:
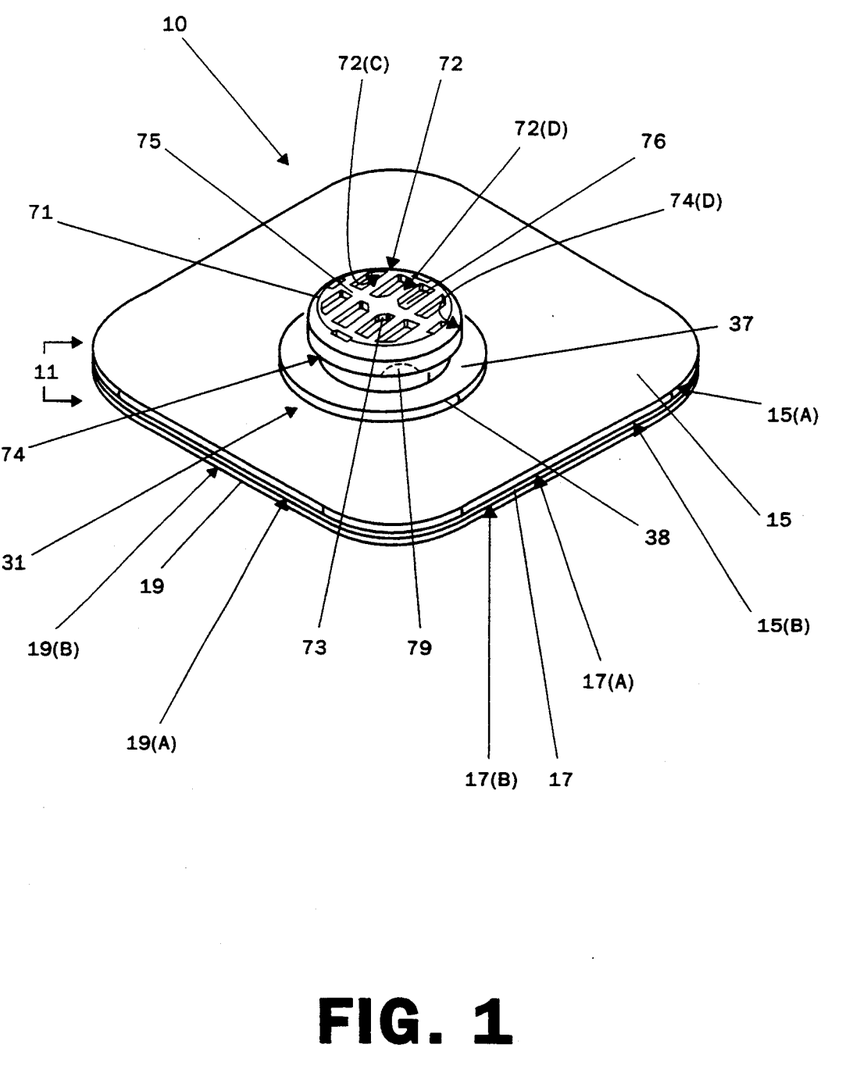
FIG. 1 is a perspective outer view of a preferred embodiment (in closed position) of the noninvasive device for preventing pressure build-up in pleural space and reducing possibility of development of a tension pneumothorax from an open pneumothorax, embodying the principles of the invention.
Figure 3:
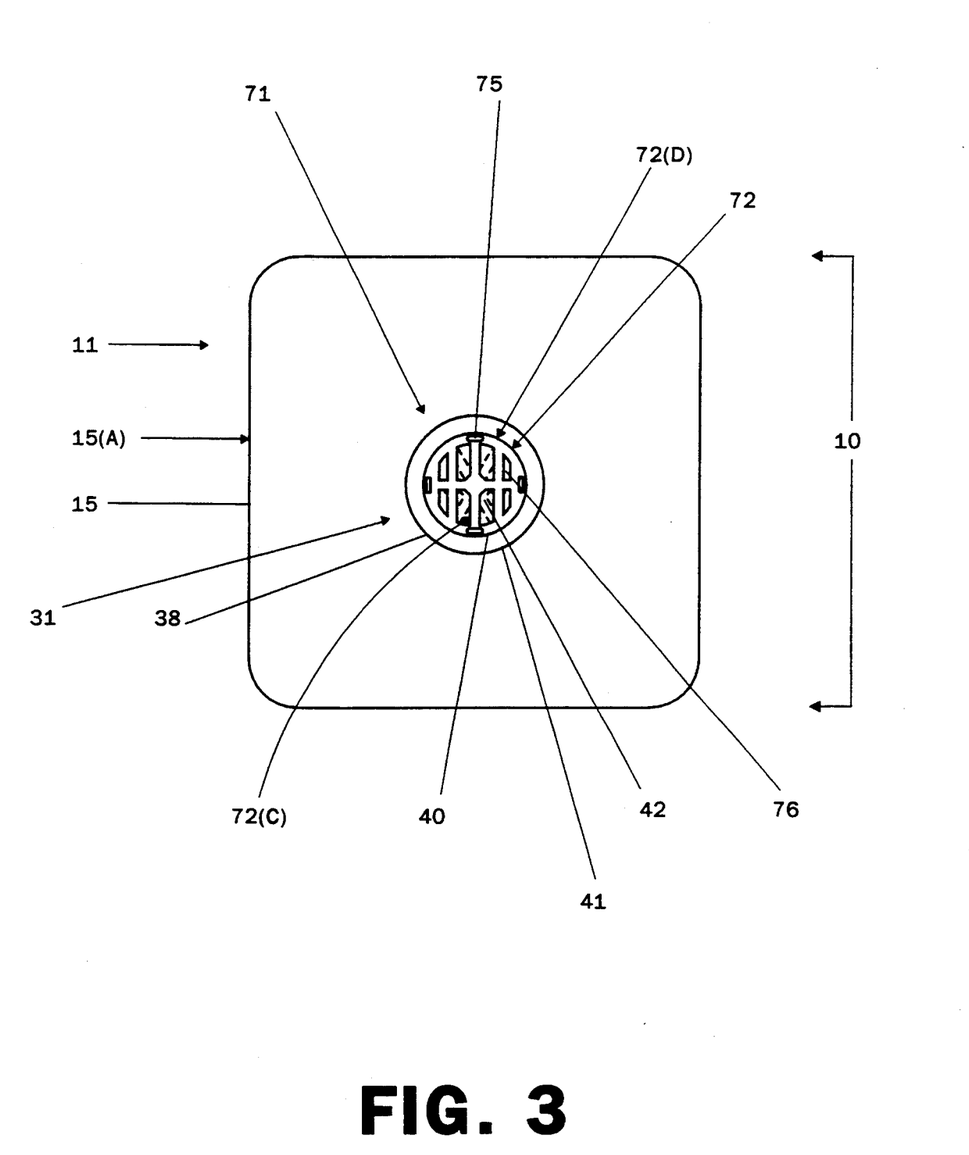
FIG. 3 is a top plan view of the invention (in closed position)

The protective, tubular cover 71 most preferably comprises a top surface 72 and a tubular surface 74. Each of the top surface 72 and the tubular surface 74 has an inside surface (C) and an outside surface (D). The top surface 72 preferably has a screening means 75 and a small, tubular, central, vertical, inward extension 73 from the inside surface 72(C) of the top surface 72. The screening means 75 comprises a number of openings 76 to allow substantially unrestricted discharge flow of air, body fluids or any combination thereof passing through the check valve 51 in order to prevent any build-up of air, body fluids or any combination thereof. Blood clogging, for example, has been a problem in the past in similar apparatus, due to size of openings in previous patents. In the present invention, in case of blood clogging, the cover 71 may be easily removed, cleaned and replaced, without effecting the inflow of air to a noticeable extent.

Preferably, the tubular surface 74 may have equally-distanced small bumps 79 located on the inside surface 74(C) of the tubular surface 74. Most preferably, the central hole 53 of the generally flat, one-way check valve 51 may be first positioned in the small, central post 43 on the middle part 41 of the tubular base 31. The small, central post 43 on the middle part 41 of the tubular base 31 may be then preferably positioned inside of the small, tubular, vertical, inward extension 73 from the top surface 72 of the tubular cover 71. Finally, the equally-distanced small bumps 79 of the tubular cover 71 may be preferably positioned around the thin, annular rim 44 on the outside 35 of the tubular base 31, such that the tubular base 31 and the tubular cover 71 provide a protective shield for the check valve 51. If necessary, at any time the protective, tubular cover 71 of the device 10 may be preferably raised to allow cleaning or replacement of the check valve 51 or of the tubular cover 71 or both.

Figure 6:
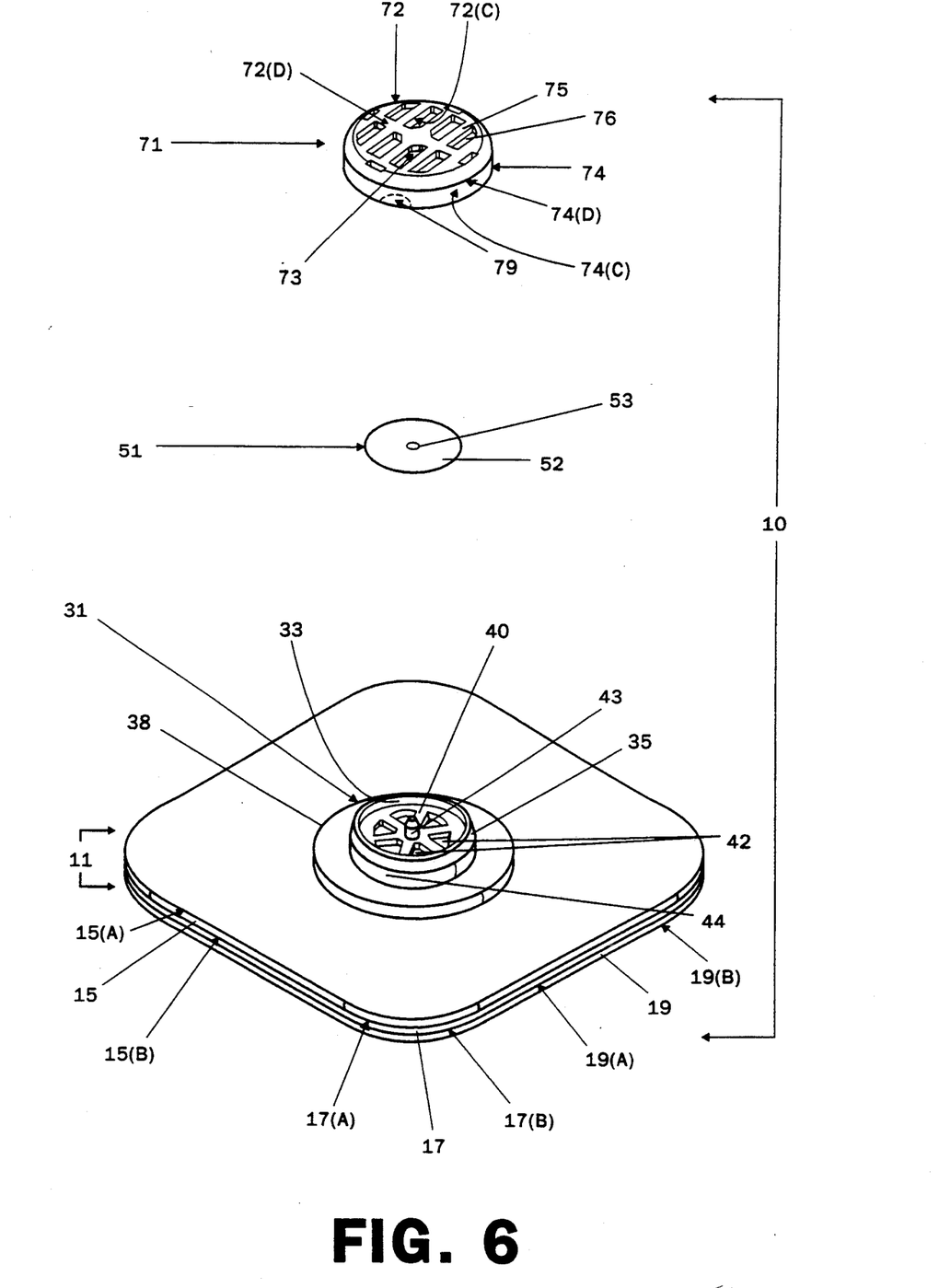
FIG. 6 is a perspective outer view of an open embodiment of the invention, with the cover removed.
Figure 7:
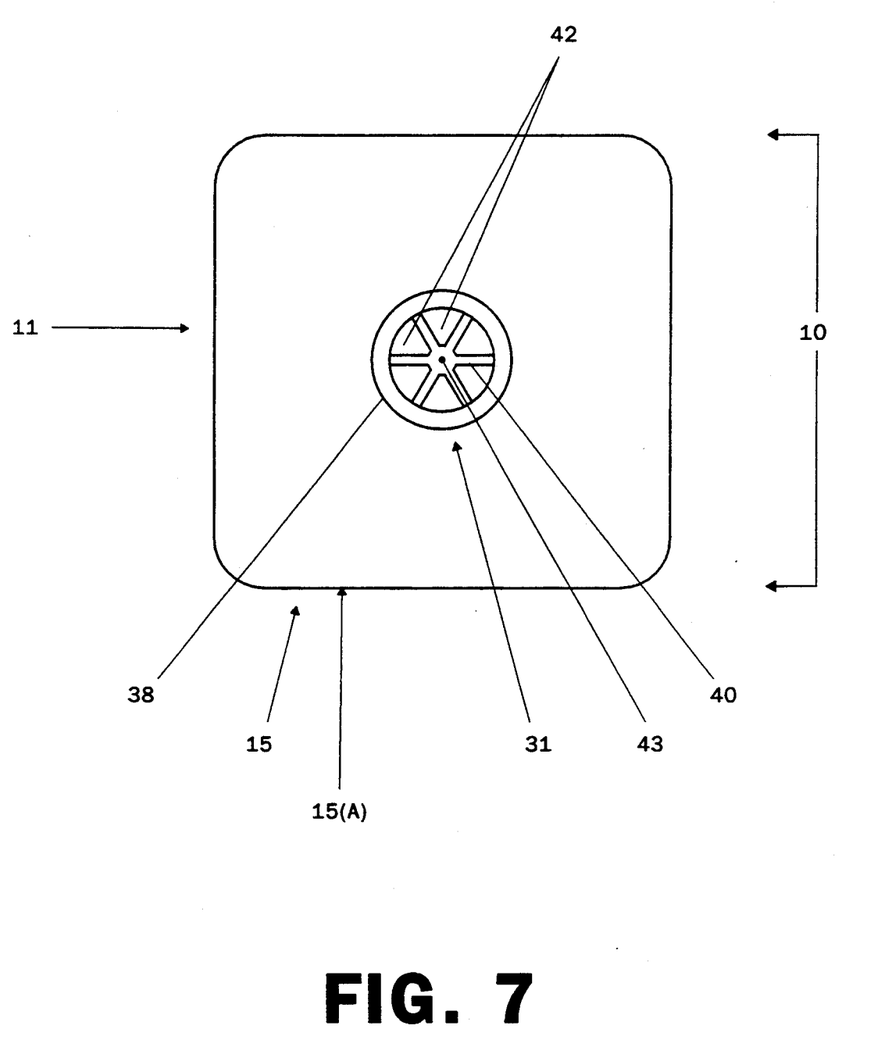
FIG. 7 is a top plan view of the invention in FIG. 6 (in open position).

In addition, the middle part 41 of the tubular base 31 may be preferably shaped like a wheel in order to facilitate discharge of air, body fluids or any combination thereof from the tubular base 31. Also, the number of openings 76 of the screening means 75 of the tubular cover 71 may most preferably be rectangular and semi-rectangular in shape and shall be in operative relationship with the check valve 51 in order to facilitate discharge of air, body fluids or any combination thereof from the device 10 after air, body fluids or any combination thereof has passed through the check valve 51. In addition to simplifying discharge of air, body fluids or any combination thereof, such shapes of the screening means 75 serve as a protective shield for the wound 91.

The protective, tubular cover 71 may preferably have four equally-distanced small bumps 79. Such bumps 79 may be easily adjusted around the thin, annular rim 44 on the outside 35 of the tubular base 31 in order to allow the protective cover 71 to rotate around the annular rim 44 and to permit variation of air, body fluids or any combination thereof.

The invention also illustrates a method for preventing pressure build-up in pleural space and reducing the possibility of the development of tension pneumothorax from an open pneumothorax by using the noninvasive device 10 described above. The method comprises removing the bottom layer 19 of the sheet 11 and placing the aperture 13 in the middle layer 17 around and in alignment with the opening 97 of the wound 91 of the patient 93. With the protective, tubular cover 71 and the tubular base 31 both comprising openings and with the check valve 51 being preferably transparent, the device 10 may be attached to the body 95 of the patient 93 such that the wound 91 may be preferably visible through the protective, tubular cover 71, through the check valve 51, and through the tubular base 31. The device 10 should be attached in a manner to facilitate and maximize the control of outflow of air, body fluids or any combination thereof through the device 10 from the tubular base 31 to and out of the protective, tubular cover 71.

The protective, tubular cover 71 may be most preferably removed for easy and quick cleaning or replacement of the check valve 51 or of the protective, tubular cover 71 or of both, at any point during operation in a minimal period of time. In addition, the protective, tubular cover 71 may comprise four equally-distanced small bumps 79 which may be easily adjusted around the thin, annular rim 44 on the outside 35 of the tubular base 31. The protective cover 71 may preferably be rotated around the annular rim 44 in order to permit discharge variation of air, body fluids or any combination thereof.

What is claimed as invention is:

1. A noninvasive device for preventing pressure build-up in pleural space and reducing possibility of development of a tension pneumothorax from an open pneumothorax or a sucking chest wound, which comprises:

a. a noninvasive, flexible, pliable sheet with a central aperture, said sheet comprising a top layer, a middle layer, and a bottom layer, with the middle layer being adjusted between the top layer and the bottom layer, each layer having a top surface and a bottom surface, the bottom surface of the middle layer covered with a temporarily adhesive material which attaches the bottom surface of the middle layer to the top surface of the bottom layer, said temporarily adhesive material allowing the top surface of the bottom layer to be easily, efficiently and quickly removable from the bottom surface of the middle layer and the bottom surface of the middle layer to be easily, efficiently and quickly adhered to and easily, efficiently and quickly removed from a body of a patient in surrounding relationship to the wound, said central aperture running in alignment through the top layer, the middle layer and the bottom layer, and the aperture being in alignment with an opening of the wound when the sheet is adhered to the body of the patient;

b. an annular flange with a top surface and a bottom surface, attached to the top surface of the middle layer of the sheet, the bottom surface of the annular flange or the top surface of the middle layer covered by an adhesive material to attach the bottom surface of the annular flange to the top surface of the middle layer;

c. a rigid, tubular base with an inside and an outside, said tubular base comprising a bottom part, a middle part and a top part, with a ring encircling the bottom part and extending horizontally from the outside of and as an integral component of the bottom part of the tubular base between the bottom surface of the top layer of the sheet and the top surface of the annular flange, such that the annular flange extends horizontally between the ring and the middle layer of the sheet, holding the tubular base vertically and upwardly in a permanent position, the bottom surface of the top layer or the top surface of the ring covered by adhesive material in order to attach the bottom surface of the top layer to the top surface of the ring; with a valve base extending across the inside of the middle part of the tubular base as an integral part of the tubular base, said valve base comprising openings to permit air, body fluids or any combination thereof to escape from the wound and a small, integral, central post extending vertically and upwardly from the valve base, and with a thin, annular rim running around the outside of the middle part of the tubular base;

d. a generally flat, one-way check valve comprising a light-weight, flat, flexible, disc with a small, central hole, said check valve located on the valve base extending inside the middle part of the tubular base, such that the small, central post extending upwardly from the valve base passes through the central hole of the check valve;

e. a protective, tubular cover comprising a top surface and a tubular surface, the top surface and the tubular surface each having an inside surface and an outside surface, said top surface having a small, tubular, central, vertical, inward extension from the inside surface of the top surface and a screening means comprising a number of openings to allow substantially unrestricted discharge flow of air, body fluids or any combination thereof passing through the check valve in order to prevent any build-up of air, body fluids or any combination thereof in the device, and said tubular surface having equally-distanced small bumps located on the inside surface of the tubular surface;

such that the central hole of the generally flat, one-way check valve is positioned in the small, central post on the middle part of the tubular base, the small, central post on the middle part of the tubular base is positioned inside of the small, tubular, vertical, inward extension from the top surface of the tubular cover, and the equally-distanced small bumps of the tubular cover are positioned around the thin, annular rim on the outside of the middle of the tubular base, such that the tubular base and the tubular cover are interlocked and provide a protective shield for the check valve.

2. The device of claim 1, wherein the protective, tubular cover is raised to allow efficient cleaning or replacement of the check valve or of the tubular cover or both.

3. The device of claim 1, wherein the middle part of the tubular base is shaped like a wheel in order to facilitate discharge of air, body fluids or any combination thereof from the tubular base.

4. The device of claim 1, wherein the screening means of the top surface of the tubular cover comprises a number of openings in rectangular and semi-rectangular shapes, said number of openings being in operative relationship with the check valve in order to facilitate discharge of air, body fluids or any combination thereof from the device after air, body fluids or any combination thereof has passed through the check valve, and to serve as a protective shield for the wound.

5. The device of claim 1, wherein the protective, tubular cover has four equally-distanced small bumps which are easily adjusted around the thin, annular rim on the outside of the tubular base, said bumps allowing the protective cover to rotate around the annular rim and permitting discharge variation of air, body fluids or any combination thereof.

6. The device of claim 1 wherein the sheet comprises four edges and four curved corners.

7. The device of claim 1 wherein the annular flange is removed from under the ring of the tubular base.

8. A method for preventing pressure build-up in pleural space and reducing possibility of development of tension pneumothorax from an open pneumothorax or a sucking chest wound by using a noninvasive device which comprises:

a. a noninvasive, flexible, pliable sheet with a central aperture, said sheet comprising a top layer, a middle layer, and a bottom layer, with the middle layer being adjusted between the top layer and the bottom layer, each layer having a top surface and a bottom surface, the bottom surface of the middle layer covered with a temporarily adhesive material which attaches the bottom surface of the middle layer to the top surface of the bottom layer, said temporarily adhesive material allowing the top surface of the bottom layer to be easily, efficiently and quickly removable from the bottom surface of the middle layer and the bottom surface of the middle layer to be easily, efficiently and quickly adhered to and easily, efficiently and quickly removed from a body of a patient in surrounding relationship to the wound, said central aperture running in alignment through the top layer, the middle layer and the bottom layer, and the aperture being in alignment with an opening of the wound when the sheet is adhered to the body of the patient;

b. an annular flange with a top surface and a bottom surface, attached to the top surface of the middle layer of the sheet, the bottom surface of the annular flange or the top surface of the middle layer covered by an adhesive material to attach the bottom surface of the annular flange to the top surface of the middle layer;

c. a rigid, tubular base with an inside and an outside, said tubular base comprising a bottom part, a middle part and a top part, with a ring encircling the bottom part and extending horizontally from the outside of and as an integral component of the bottom part of the tubular base between the bottom surface of the top layer of the sheet and the top surface of the annular flange, such that the annular flange extends horizontally between the ring and the middle layer of the sheet, holding the tubular base vertically and upwardly in a permanent position, the bottom surface of the top layer or the top surface of the ring covered by adhesive material in order to attach the bottom surface of the top layer to the top surface of the ring; with a valve base extending across the inside of the middle part of the tubular base as an integral part of the tubular base, said valve base comprising openings to permit air, body fluids or any combination thereof to escape from the wound and a small, integral, central post extending vertically and upwardly from the valve base, and with a thin, annular rim running around the outside of the middle part of the tubular base;

d. a generally flat, one-way check valve comprising a light-weight, flat, flexible, disc with a small, central hole, said check valve located on the valve base extending inside the middle part of the tubular base, such that the small, central post extending upwardly from the valve base passes through the central hole of the check valve;

e. a protective, tubular cover comprising a top surface and a tubular surface, the top surface and the tubular surface each having an inside surface and an outside surface, said top surface having a small, tubular, central, vertical, inward extension from the inside surface of the top surface and a screening means comprising a number of openings to allow substantially unrestricted discharge flow of air, body fluids or any combination thereof passing through the check valve in order to prevent any build-up of air, body fluids or any combination thereof in the device, and said tubular surface having equally-distanced small bumps located on the inside surface of the tubular surface; such that the central hole of the flat check valve is positioned in the small, central post on the middle part of the tubular base, the small central post on the middle part of the tubular base is positioned inside of the small, tubular, vertical extension from the top surface of the tubular cover, and the equally-distanced small bumps of the tubular cover are positioned around the thin, annular rim on the outside of the middle of the tubular base, such that the tubular base and the tubular cover are interlocked and provide a protective shield for the check valve;

said method comprising removing the bottom layer of the sheet and placing the aperture in the middle layer around and in alignment with the opening of the wound of the patient such that the one-way check valve is visible through the protective cover in order to control flow of air, body fluids or any combination thereof through the device from the tubular base to and out of the protective cover.

9. The method of claim 8, wherein the protective, tubular cover is removed for cleaning or replacement of the check valve or of the tubular cover or both, at any point during operation in a minimal period of time.

10. The method of claim 8, wherein the protective, tubular cover comprising four equally-distanced small bumps which are easily adjusted around the thin, annular rim on the outside of the tubular base, said bumps allowing the protective cover to rotate around the annular rim and permitting discharge variation of air, body fluids or any combination thereof.

11. The method of claim 8, wherein the annular flange is removed from under the ring of the tubular base.

* * * * *